United States Patent
Zhao et al.

(10) Patent No.: US 10,125,164 B2
(45) Date of Patent: Nov. 13, 2018

(54) PROCESS FOR PREPARING D-ARGINYL-2,6-DIMETHYL-L-TYROSYL-L-LYSYL-L-PHENYLALANINAMIDE

(71) Applicant: FLAMMA S.P.A., Chignolo d'Isola (IT)

(72) Inventors: Xinjun Zhao, Dalian (CN); Minyu Zheng, Dalian (CN); Xiaozhong Yu, Shenyang (CN); Hanrong Gao, Dalian (CN); Fabrice Cornille, Buress sur Yvette (FR)

(73) Assignee: FLAMMA S.P.A., Chignolo d'Isola (IT)

( * ) Notice: Subject to any disclaimer, the term of this patent is extended or adjusted under 35 U.S.C. 154(b) by 31 days.

(21) Appl. No.: 15/319,858

(22) PCT Filed: Jun. 24, 2015

(86) PCT No.: PCT/EP2015/064301
§ 371 (c)(1),
(2) Date: Dec. 19, 2016

(87) PCT Pub. No.: WO2015/197723
PCT Pub. Date: Dec. 30, 2015

(65) Prior Publication Data
US 2017/0129920 A1    May 11, 2017

Related U.S. Application Data

(60) Provisional application No. 62/016,783, filed on Jun. 25, 2014.

(51) Int. Cl.
| | | |
|---|---|---|
| *C07K 5/11* | (2006.01) | |
| *C07K 5/087* | (2006.01) | |
| *C07K 5/068* | (2006.01) | |
| *C07K 5/062* | (2006.01) | |

(52) U.S. Cl.
CPC ........ *C07K 5/1019* (2013.01); *C07K 5/06034* (2013.01); *C07K 5/06086* (2013.01); *C07K 5/0812* (2013.01)

(58) Field of Classification Search
CPC ............ C07K 5/06034; C07K 5/06086; C07K 5/0812; C07K 5/1019
See application file for complete search history.

(56) References Cited

U.S. PATENT DOCUMENTS

| | | | | |
|---|---|---|---|---|
| 9,982,014 | B2 * | 5/2018 | Hirai | C07K 5/1021 |
| 2016/0340389 | A1 * | 11/2016 | Wilson | C07K 5/1019 |
| 2017/0152289 | A1 * | 6/2017 | Zhao | C07K 5/0812 |

FOREIGN PATENT DOCUMENTS

| | | |
|---|---|---|
| EP | 0190597 A2 | 8/1986 |
| WO | 2007027742 A2 | 3/2007 |
| WO | 2013086020 A1 | 6/2013 |
| WO | 2015060462 A1 | 4/2015 |
| WO | 2015100376 A1 | 7/2015 |

OTHER PUBLICATIONS

Reddy et al. Synthesis and Pharmacological Evaluation of Highly Potent [Dmt1]DALDA Analogs. Adv Exp Med Biol. 2009; 611: 473-474. (Year: 2009).*
Search Report and Written Opinion of PCT/EP2015/064301 dated Sep. 15, 2015.

* cited by examiner

*Primary Examiner* — Marcela M Cordero Garcia
(74) *Attorney, Agent, or Firm* — Silvia Salvadori, P.C.; Silvia Salvadori

(57) ABSTRACT

The invention relates to a process for solution-phase synthesis of D-Arginyl-2,6-dimethyl-L-tyrosyl-L-lysyl-L-phenylalaninamide, an active ingredient used for both common and rare diseases including a mitochondrial targeted therapy for ischemia reperfusion injury.

14 Claims, No Drawings

PROCESS FOR PREPARING D-ARGINYL-2,6-DIMETHYL-L-TYROSYL-L-LYSYL-L-PHENYLALANINAMIDE

This application is a U.S. national stage of PCT/EP2015/064301 filed on 24 Jun. 2015, which claims priority to and the benefit of U.S. Provisional Application Ser. No. 62/016,783 filed on 25 Jun. 2014, the contents of which are incorporated herein by reference in their entireties.

TECHNICAL FIELD

The invention relates to a process for solution-phase synthesis of D-Arginyl-2,6-dimethyl-L-tyrosyl-L-lysyl-L-phenylalaninamide (abbreviated H-D-Arg-(2,6-Dimethyl) Tyr-L-Lys-L-Phe-NH$_2$, development code SS-31, MTP-131, RX-31) of Formula (I), an active ingredient developed by Stealth BioTherapeutics under the investigational drug brand names Bendavia® and Ocuvia®, for both common and rare diseases including a mitochondrial targeted therapy for ischemia reperfusion injury.

Formula (I)

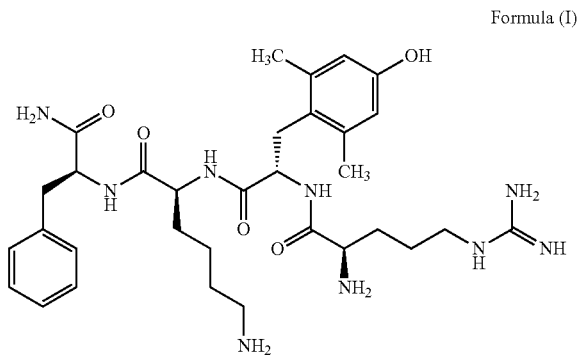 [SMILES: Cc1cc(O)cc(C)c1C[C@H](NC(=O)[C@H](N)CCCNC(=N)N)C(=O)N[C@@H](CCCCN)C(=O)N[C@@H](Cc1ccccc1)C(N)=O]

BACKGROUND

The product belongs to the class of so-called "Szeto-Schiller peptides". Szeto-Schiller peptides or "SS peptides" are small, aromatic-cationic, water soluble, highly polar peptides, such as disclosed in U.S. Pat. No. 6,703,483 and U.S. Pat. No. 7,576,061, which can readily penetrate cell membranes. The aromatic-cationic peptides include a minimum of two amino acids, and preferably include a minimum of four amino acids, covalently joined by peptide bonds. The maximum number of amino acids is about twenty amino acids covalently joined by peptide bonds. As described by EP 2012/2436390, optimally, the number of amino acids present in the SS peptides is four.

Bendavia® is being tested for the treatment of ischemia reperfusion injury in patients with acute myocardial infarction (AMI), for the treatment of acute kidney injury (AKI) and renal microvascular dysfunction in hypertension, for the treatment of skeletal muscle dysfunction, for the treatment of mitochondrial myopathy and for the treatment of chronic heart failure. Trials are ongoing to assess the Ocuvia's potential to treat Leber's Hereditary Optic Neuropathy (LHON) a devastating inherited disease that causes sudden blindness, often in young adults.

Mitochondria are the cell's powerhouse, responsible for more than 90% of the energy our bodies need to sustain life and support growth. The energetics from mitochondria maintains healthy physiology and prevents disease. In many common and rare diseases, dysfunctional mitochondria are a key component of disease progression.

D-Arginyl-2,6-dimethyl-L-tyrosyl-L-lysyl-L-phenylalaninamide is a cell-permeable and mitochondria-targeted peptide that showed antioxidant activity and was concentrated in the inner mitochondrial membrane. Compound (<1 nM) significantly reduced intracellular reactive oxygen species, increased mitochondrial potential and prevented tBHP-induced apoptosis in both N2A and SH-SY5Y neuronal cell lines. In rats, intraperitoneal treatment (1 and 3 mg/kg) 1 day prior to unilateral ureteral obstruction and every day thereafter for 14 days significantly decreased tubular damage, macrophage infiltration and interstitial fibrosis. Compound (3 mg/kg i.p. qd for 2 weeks) also prevented apoptosis and insulin reduction in mouse pancreatic islets caused by streptozotocin.

Further studies performed in a G93A mouse model of amyotrophic lateral sclerosis (ALS) demonstrated that the compound (5 mg/kg/day i.p. starting at 30 days of age) led to a significant delay in disease onset. Potentially useful for the treatment of ALS and may be beneficial in the treatment of aging and diseases associated with oxidative stress.

In the last few years the peptide H-D-Arg-(2,6-Dimethyl) Tyr-L-Lys-L-Phe-NH$_2$ and its therapeutic activity have been disclosed and claimed by in several patent applications.

EP 2436390, US 20110245182 and US 20110245183 claim topical anesthetic compositions for application to the skin for pain management or anti-skin aging agents, respectively, comprising Szeto-Schiller peptides; SS-31 is specifically claimed as active ingredient. Sequence of solid-phase synthesis is indicated as the preferred preparation process.

U.S. Pat. No. 7,718,620 claims a process of treating or preventing ischemia-reperfusion injury of the kidney in a mammal by administrating an effective amount of an aromatic-cationic peptide. SS-31 is specifically claimed as active ingredient.

WO2005/001023 discloses a generical process and carrier complexes for delivering molecules to cells comprising a molecule and an aromatic cationic peptide of type D-Arg-Dmt-Lys-Phe-NH$_2$. The tetrapeptide SS-31 is specifically claimed as product useful for the process at claim 18.

WO2012/174117 and WO2014/210056 claim therapeutic compositions based on SS peptides and the aromatic-cationic peptide D-Arg-Dmt-Lys-Phe-NH$_2$ as active agent.

WO 2013/086020, WO 2004/070054 and WO 2005/072295 provide processes for preventing mithochondrial permeability transition and reducing oxidative damage in a mammal, a removed organ, or a cell in need thereof and specifically claims the process wherein the peptide does not have mu-opioid receptor agonist activity, i.e., D-Arg-Dmt-Lys-Phe-NH$_2$.

WO 2009/108695 discloses a process for protecting a kidney from renal injury which may be associated with decreased or blocked blood flow in the subject's kidney or exposure to a nephrotoxic agent, such as a radiocontrast dye. The processes include administering to the subject an effective amount of an aromatic-cationic peptide to a subject in need thereof and one of the selected peptide is D-Arg-Dmt-Lys-Phe-NH$_2$.

U.S. Pat. No. 6,703,483 discloses a detailed procedure for the preparation of novel analogs of DALDA [H-Tyr-D-Arg-Phe-Lys-NH$_2$], namely H-Dmt-D-Arg-Phe-Lys-NH$_2$ using the solid-phase techniques and p-methylbenzhydrylamine resin and protocols that have been extensively used by inventor's laboratory.

Most prior art processes for preparing the compound typically comprise conventionally performed peptide solid-phase synthesis with further purification by chromatography in order to obtain the requested purity for therapeutic use.

It is well known that solid-phase synthesis followed by chromatographic purification is time consuming, very expensive and very difficult to be scaled up on industrial scale, so the need of developing a process for large scale production is obvious. The compound is isolated as organic acid salt, as acetate or trifluoro acetate.

Reddy et al., *Adv. Exp. Med. Biol.,* 2009, 611, 473 generally describes the liquid-phase synthesis of antioxidant peptides and similar others (SS-02, SS-20), involving routinely used side chain protecting groups for amino acid building blocks. The guanidine group was protected with $NO_2$ and the $\varepsilon$-$NH_2$ of Lys was protected by Cbz or 2-Cl-Cbz. These peptides were synthesized using Boc/Cbz chemistry and BOP reagent coupling. Starting with the C-terminal Lys residue protected as H-Lys(2-Cl-Cbz)-$NH_2$, (prepared from the commercially available Boc-Lys(2-Cl-Cbz)-OH in two steps by amidation with $NH_4HCO_3$ in the presence of DCC/HOBt following a literature procedure [Ueyama et all, *Biopolymers,* 1992, 32, 1535, PubMed: 1457730], followed by exposure to TFA). Selective removal of the 2-Cl-Cbz in the presence of the $NO_2$ group was accomplished using catalytic transfer hydrogenolysis (CTH) [Gowda et al., *Lett. Pept. Sci.,* 2002, 9, 153].

A stepwise procedure by standard solution peptide synthesis for preparation of potent μ agonist [Dmt]DALDA and its conversion into a potent δ antagonist H-Dmt-Tic-Phe-Lys(Z)-OH by substitution of D-Arg with Tic to enhance the δ opioid agonist activity is described by Balboni et al., *J. Med. Chem.,* 2005, 48, 5608. A general synthetic procedure for a similar tetrapeptide ([Dmt-D-Arg-Phe-Lys-$NH_2$ is described by Ballet et al., *J. Med. Chem.* 2011, 54, 2467.

Similar DALDA analog tetrapeptides were prepared by the manual solid-phase technique using Boc protection for the α-amino group and DIC/HOBt or HBTU/DIEA as coupling agent [Berezowska et al., *J. Med. Chem.,* 2009, 52, 6941; Olma et al., *Acta Biochim. Polonica,* 2001, 48, 4, 1121; Schiller at al., Eur. J. Med. Chem., 2000, 35, 895].

Despite the high overall yield in the solid-phase approach, it has several drawbacks for the scale-up process such as:
 a. the application of the highly toxic and corrosive hydrogen fluoride for cleavage of the peptide from the resin,
 b. low loading (0.3-0.35 mmol/g of resin) proved necessary for successful end-step, and
 c. use of excess amounts of reagents (3-fold of DIC, 2.4-fold of HOBt, etc.) on each step [Ryakhovsky et al., Beilstein J. Org. Chem., 2008, 4(39), 1, doi: 10.376/bjoc.4.39]

SUMMARY

The invention relates to a more efficient process avoiding either solid-phase synthesis or chromatographic purification, more suitable for large scale production. The process of the invention is described in Scheme A.

The following abbreviations are used:
Dmt=2,6-dimethyl tyrosine; Z=benzyloxycarbonyl; $MeSO_3H$=methanesulphonic acid; Boc=Tert-butyloxycarbonyl; NMM=N-methyl morpholine; TB TU=N,N,N',N'-Tetramethyl-O-(benzotriazol-1-yl)uronium tetrafluoroborate; DMF=dimethyl formamide; TFA=trifluoroacetic acid Scheme A shows the process for the solution phase synthesis of peptide 1 for assembly of the tetrapeptide backbone using O-Benzyl (Bzl) group and benzyloxycarbonyl (Z) group respectively, as the temporary protection for amino acids' N-termini, followed by a final catalytic hydrogenolysis. The final product is isolated as organic acid salt, for example, acetic acid salt.

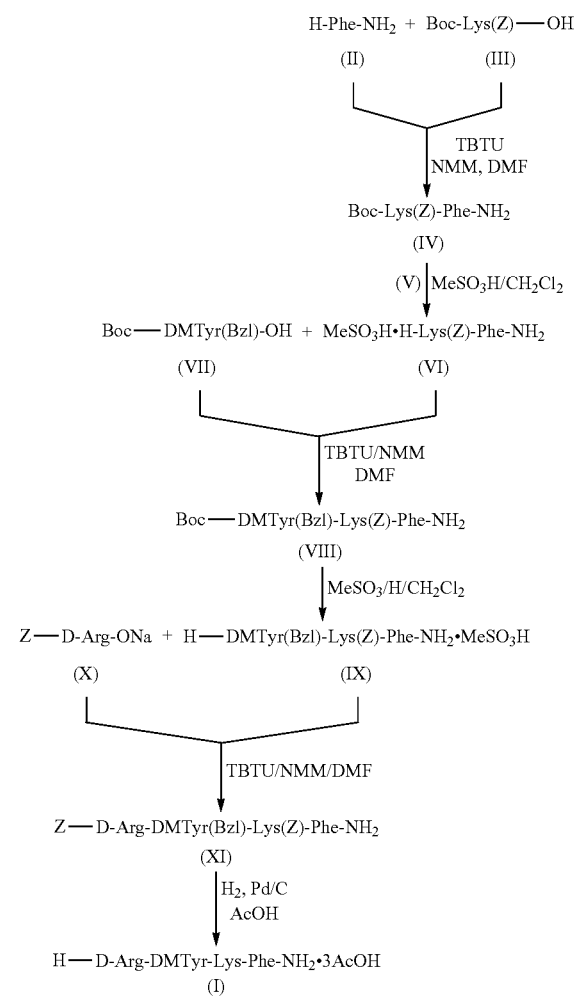

Scheme A

This process is a notable improvement with respect to the prior art and its advantages can be summarized as follows:
 The synthesis is performed in liquid phase allowing the scale up on industrial scale without need of special equipment;
 The selection of the protecting group in the building blocks allows a straightforward synthesis with very simple deprotection at each step and minimize the formation of undesired by-product;
 Each intermediate can be crystallized allowing removal of impurities which are not transferred to the following step;
 The purity of each intermediate is very high and usually close to 99%.

DETAILED DESCRIPTION

The present invention provides, in a first aspect, a novel and efficient process that leads to a SS-31 salt, especially the acetic acid salt, which is convenient for the industrial scale and provides the desired product in good yields. In particular, the inventors found that SS-31 acetate salt can be advantageously obtained with a process, in which the overall deprotection step is the n−1 step of the process.

Accordingly, it is an object of the present invention to provide a process for preparing H-D-Arg-Dmt-Lys-Phe-NH$_2$ of formula (I) as the acetic acid salt.

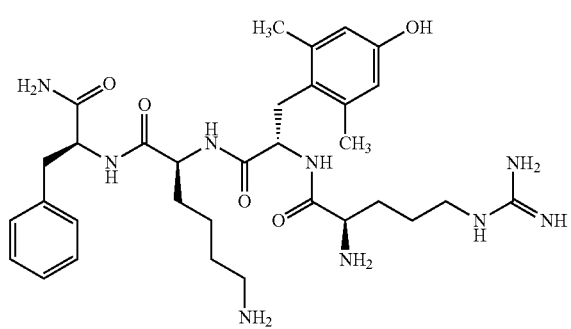

(I)

which comprises the steps of:
coupling compound (II) H-Phe-NH$_2$:

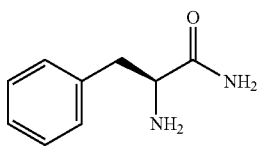

(II)

with compound (III) Boc-Lys(Z)-OH:

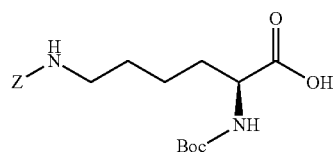

(III)

to obtain a compound of formula (IV), Boc-Lys(Z)-Phe-NH$_2$:

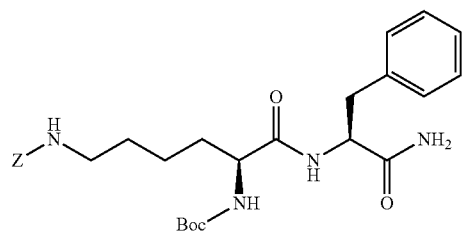

(IV)

and
reacting compound (IV) with methanesulfonic acid (V)

MeSO$_3$H (V)

to obtain the free amine salt (VI) MeSO$_3$H.H-Lys(Z)-Phe-NH$_2$:

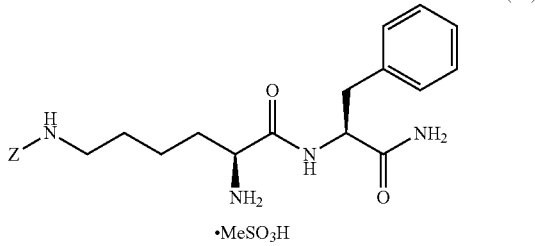

(VI)

The salt (VI) is reacted with the protected amino acid Boc-Dmt(Bzl)-OH (VII)

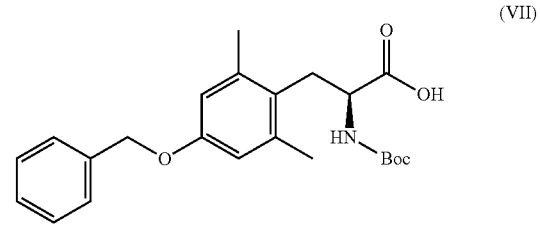 [SMILES: Cc1cc(OCc2ccccc2)cc(C)c1C[C@H](NC(=O)OC(C)(C)C)C(=O)O]

(VII)

to obtain the protected tripeptide (VIII):

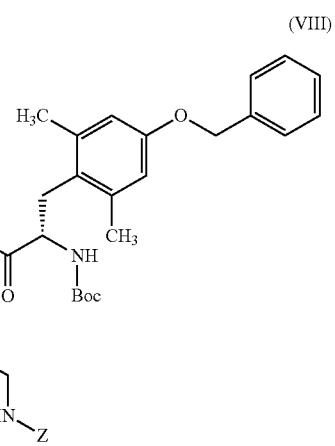

(VIII)

which is treated with methanesulfonic acid (V) to obtain the corresponding salt (IX), MeSO$_3$.H-Dmt(Bzl)-Lys(Z)-Phe-NH$_2$:

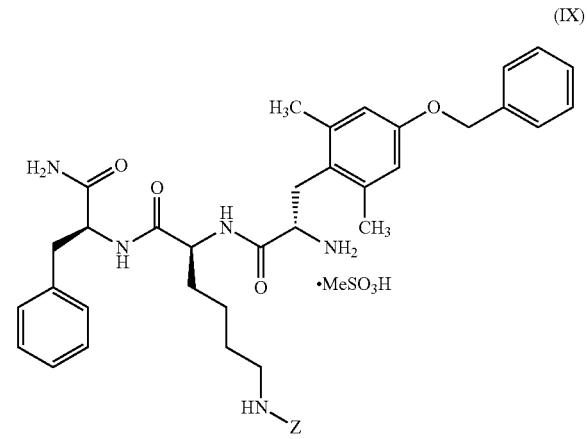

(IX)

The acid salt (IX) is coupled with Z-D-Arg-ONa (X)

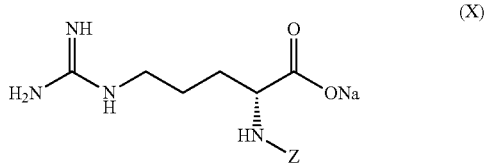

to form the protected tetrapeptide (XI), Z-D-Arg-Dmt(Bzl)-Lys(Z)-Phe-NH$_2$:

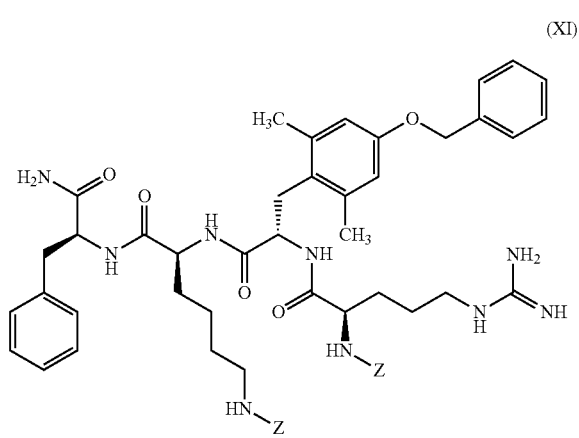

The tetrapeptide (I) is obtained by hydrogenolysis of (XI) and further reacted with acetic acid to form the corresponding salt.

In one embodiment of the process, the coupling between (II) and (III) is performed in the presence of N,N,N',N'-tetramethyl-O-(benzotriazol-1-yl)uronium tetrafluoroborate (known as TBTU) and an organic base belonging to the class of tertiary amines such as NMM, triethylamine and diisopropylethylamine as well as a polar solvent such as DMF, acetonitrile, tetrahydrofuran (THF), 2-methyl-tetrahydrofuran (ME-THF) etc.

In one embodiment, the coupling between (II) and (III) is performed in a temperature range between 0° C. and 60° C., preferably between 20° C. and 30° C.

In another embodiment, the formation of methanesulfonic salt (VI) is obtained in methylene chloride as solvent and crystallized from the same solvent. Other solvents suitable for crystallization are THF, ethyl acetate and acetonitrile.

In one embodiment of process the coupling reaction between compound (VI) and compound (VII) is performed in the presence of N,N,N',N'-tetramethyl-O-(benzotriazol-1-yl)uronium tetrafluoroborate (known as TBTU) and a base of tertiary amine class such as N-methyl morpholine (NMM), triethylamine and diisopropylethylamine as well as a polar solvent as DMF, acetonitrile, THF, 2-ME-THF etc.

In another embodiment, the formation of methanesulfonic salt (IX) is obtained in methylene chloride as solvent and crystallized from the same solvent. Other suitable solvents for crystallization are THF, ethyl acetate and acetonitrile.

In one embodiment of process the coupling reaction between compound (IX) and compound (X) is performed in the presence of N,N,N',N'-tetramethyl-O-(benzotriazol-1-yl) uronium tetrafluoroborate (known as TBTU) and a base of tertiary amine class such as NMM, triethylamine and diisopropylethylamine as well as a polar solvent as DMF, acetonitrile, THF, 2-ME-THF etc.

In one embodiment the hydrogenolysis of (XI) is performed with heterogeneous catalyst Pd on C and acetic acid as solvent. Other suitable catalysts are Pd(OH)$_2$ on carbon, Pd (and or PdCl$_2$) on SiO$_2$, Al$_2$O$_3$ or polymer, and solvents such as methanol, ethanol, isopropanol, DMF, THF and acetonitrile.

The intermediates can be isolated or not from the reaction mixture.

In one aspect of the process, the intermediates (IV), (VI), (VIII), (IX) and (XI) are isolated and crystallized. When the intermediates are isolated, their purity exceeds 98%.

In one preferred aspect, the crystallization of intermediate (VIII), Boc-Dmt(Bzl)-Lys(Z)-Phe-NH$_2$ is able to avoid the transfer of a critical impurity to the following process steps.

In one preferred aspect, the critical impurity is compound (XII), H-D-Dmt(Bzl)-Lys(Z)-Phe-NH$_2$.

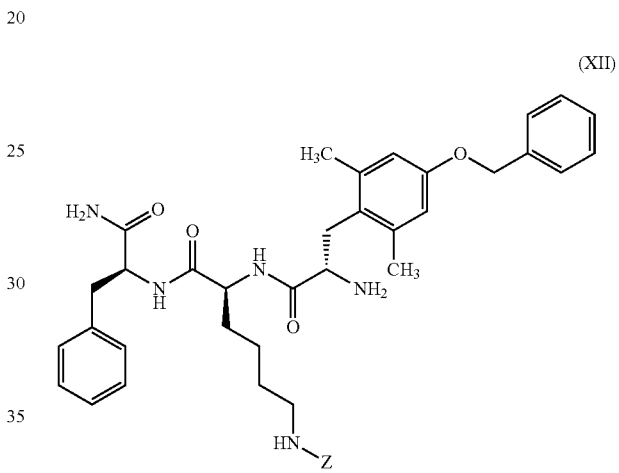

In another preferred aspect, the crystallization process for the protected tetrapeptide (XI), Z-D-Arg-Dmt(Bzl)-Lys(Z)-Phe-NH$_2$ allows to obtain the product as a solid with a purity close to 99%.

In another preferred aspect, the final deprotection is performed by simple hydrogenation and allows to obtain the final product in solid form of acetate salt after simple crystallization without any need of HPLC purification or any freeze-drying, a purification and isolation process extremely expensive but commonly used in the manufacture of peptide as drug.

In a preferred aspect, the process allows to scale-up an efficient process to obtain the peptide as a solid which can be used in formulation as such or can be easily converted in any other salt if required. The purity of the obtained final compound is higher than 98.5%, usually 99% and each impurity is close to 0.2% or below.

EXAMPLES

Example 1: Preparation of Boc-Lys(Z)-Phe-NH$_2$

Charge 200 mL of DMF, 44 g of Boc-Lys(Z)-OH and 15.6 g of H-Phe-NH$_2$ in a flask. Stir the mixture at room temperature for 10 min. Add 19.2 g of N-methylmorpholine and 32.1 g of TBTU successively at room temperature. Stir the mixture at room temperature for 1 h. Add 500 mL of water into the reaction mixture to precipitate the product at room temperature. Filter the mixture to isolate the solid product and wash the filter cake with water. Transfer the filter cake into a flask containing 360 mL of ethyl acetate and heat the mixture at 50° C. till all the solid is dissolved. Separate the organic phase of product and discard the small aqueous phase. Concentrate the organic phase at 40~45° C. and under vacuum to remove the solvent till lots of solid is formed. Filter the residue to isolate the solid product. Transfer the filter cake into a flask containing 2000 mL of MTBE and heat the mixture at refluxing for 20 min. Then, cool down the mixture to room temperature. Filter the mixture to isolate the solid product. Dry the filter cake at 30° C. and under vacuum to give 35 g of solid product.

Example 2: Preparation of H-Lys(Z)-Phe-NH$_2$.MeSO$_3$H

Charge 26.3 g of Boc-Lys(Z)-Phe-NH$_2$, 200 mL of methylene chloride and 9.6 g of methanesulfonic acid. Stir the mixture at 15~20° C. for 18 h. Add 100 mL of MTBE into the mixture and stir at 15~20° C. for 1 h. Filter the mixture to isolate the solid product. Dry the wet cake in air at room temperature to give 26.4 g of white solid product.

Example 3: Preparation of Boc-DMeTyr(Bzl)-Lys(Z)-Phe-NH$_2$

Charge 8.4 g of Boc-DMeTyr(Bzl)-OH, 11 g of H-Lys(Z)-Phe-NH$_2$.MeSO$_3$H, 7.4 g of TBTU and 80 mL of THF in a flask. Stir the mixture at room temperature for 15 min, and then cool down to 10° C. Add 6.36 g of N-methylmorpholine and stir the mixture at 20-25° C. for 3 h. Add the reaction mixture into a flask containing 240 mL of water. Add 32 mL of methylene chloride into the mixture obtained in the previous operation of. Stir the resultant mixture at room temperature for 20 min. Filter the mixture to isolate the solid product and wash the filter cake with acetone (300 mL×2). Dry the filter cake in air at room temperature to give 14.3 g of white solid product.

Example 4: Preparation of H-DMeTyr(Bzl)-Lys(Z)-Phe-NH$_2$.MeSO$_3$H

Charge 14 g of Boc-BMeTyr(Bzl)-Lys(Z)-Phe-NH$_2$, 280 mL of methylene chloride and 3.3 g of methanesulfonic acid in a flask. Stir the mixture at 18~22° C. for 10 h. Add 560 mL of heptanes into the mixture and stir the mixture at room temperature for 30 min. Filter the mixture to isolate the solid product. Dry the wet cake in air at room temperature to give 14 g of white solid product.

Example 5: Preparation of Z-D-Arg-DMeTyr(Bzl)-Lys(Z)-Phe-NH$_2$

Charge 6.34 g of Z-D-Arg-ONa, 100 mL of DMF and 2.0 g of methanesulfonic acid in a flask. Stir the mixture at room temperature till a clear solution was formed. Add 14 g of H-DMeTyr(Bzl)-Lys(Z)-Phe-NH$_2$.MeSO$_3$H and cool down the mixture to 10° C. Add 6.15 g of TBTU and 9.67 g of N-methylmorpholine successively. Stir the mixture at room temperature for 4 h. Add aqueous solution of LiOH prepared by dissolving 2.9 g of LiOH.H$_2$O in 8 mL of water. Stir the mixture for 30 min. Add the resultant mixture slowly into a flask containing 420 mL of water under stirring. Add 56 mL of methylene chloride into the mixture. Filter the mixture to isolate the solid product. Transfer the filter cake into a flask containing 150 mL of acetic acid, and heat the mixture at 35~40° C. till most of the solid was dissolved. Add 450 mL of MTBE into the mixture and cool down the mixture under stirring to room temperature. Filter the mixture to isolate the solid product. Dry the filter cake in air at room temperature to give 17.3 g of the white solid product.

Example 6 Preparation of H-D-Arg-DMeTyr-Lys-Phe-NH$_2$.3AcOH

Charge 2.0 g of Z-D-Arg-DMeTyr(Bzl)-Lys(Z)-Phe-NH$_2$, 20 mL of acetic acid and 5% Pd/C catalyst (which is obtained by washing 5.0 g of 5% Pd/C containing 60% of water with 30 mL of acetic acid) in a flask. Change the atmosphere of the flask with hydrogen. Stir the mixture at room temperature and pressure of 1 atm of hydrogen for 2 h. Filter the mixture to remove the Pd/C catalyst and wash the filter cake with 10 mL of acetic acid. Combine the filtrate and washing solution and concentrate the solution at 20° C. and under vacuum to remove most the solvent. Add 100 mL of acetonitrile into the residue and stir the mixture at room temperature for 20 min. Filter the mixture to isolate the solid product. Dry the filter cake at room temperature and under vacuum to give 0.7 g of the white product.

The invention claimed is:
1. A liquid-phase process for the production of H-D-Arg-(2,6-Dimethyl)Tyr-Lys-Phe-NH2 of formula (I), in the form of the acetic acid salt,

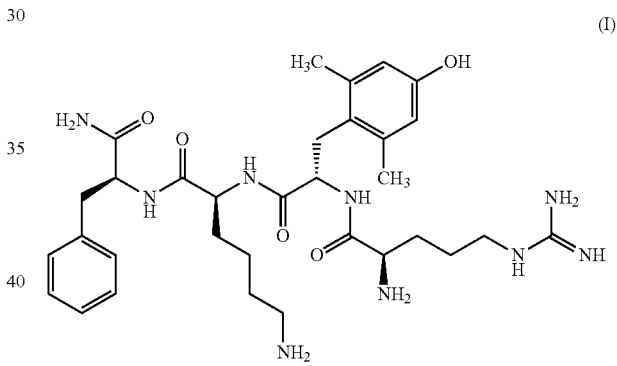

which comprises the following steps:
coupling compound (II) H-Phe-NH2:

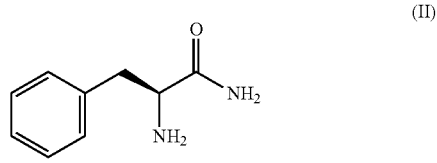

with compound (III) Boc-Lys(Z)-OH:

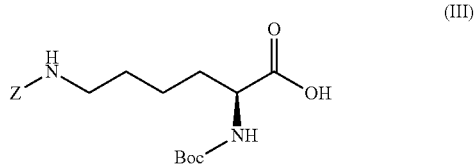

to obtain a compound of formula (IV), Boc-Lys(Z)-Phe-NH2:

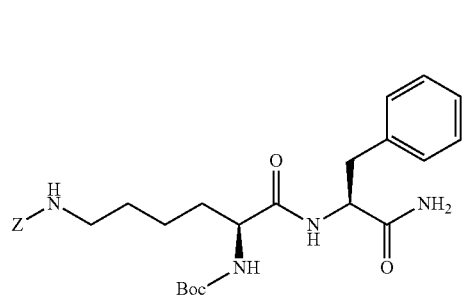
(IV)

reacting compound (IV) with methanesulfonic acid (V)

MeSO3H   (V)

to obtain the free amine salt (VI) MeSO3H.H-Lys(Z)-Phe-NH2:

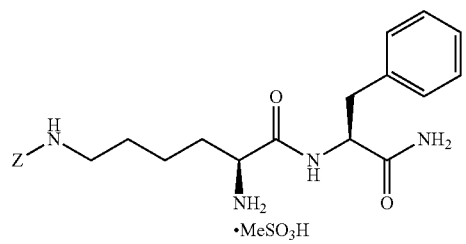
(VI)

reacting the salt (VI) with the protected amino acid Boc-Dmt(Bzl)-OH (VII)

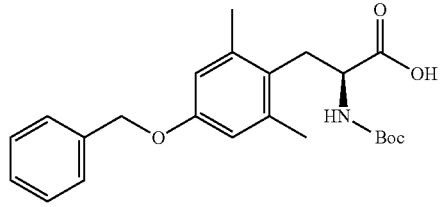
(VII)

to obtain the protected tripeptide (VIII):

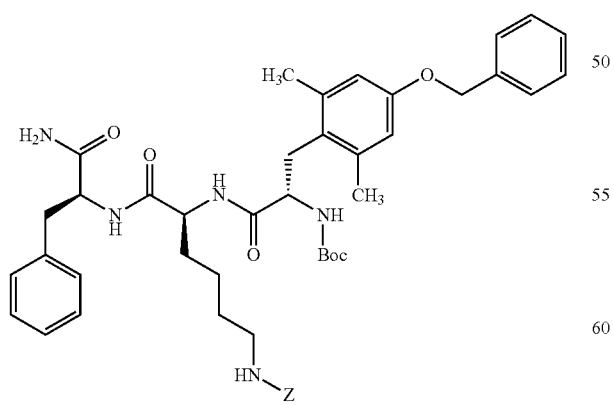
(VIII)

treating the compound (VIII) with methanesulfonic acid (V) to obtain the corresponding salt (IX), MeSO3.H-Dmt(Bzl)-Lys(Z)-Phe-NH2:

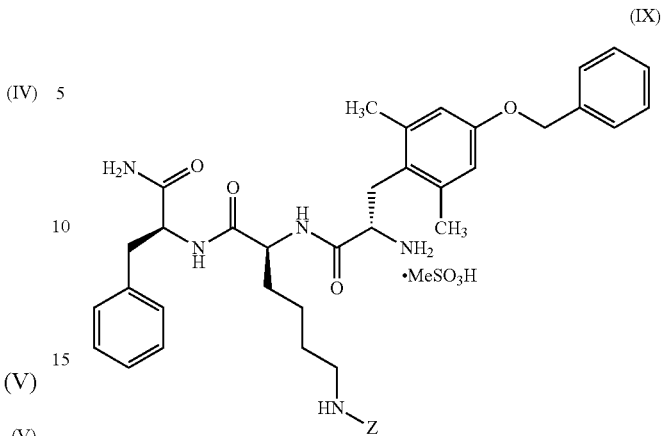
(IX)

coupling the acid salt (IX) with Z-D-Arg-ONa (X)

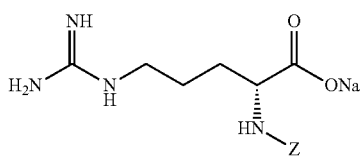
(X)

to form the protected tetrapeptide (XI), Z-D-Arg-Dmt(Bzl)-Lys(Z)-Phe-NH2:

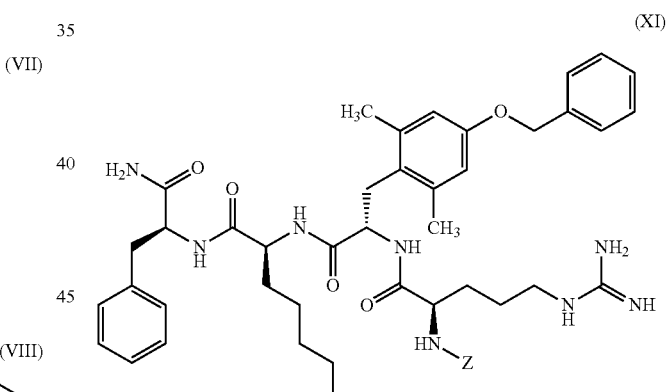
(XI)

and
deprotecting compound (XI) by hydrogenolysis to obtain the tetrapeptide H-D-Arg-(2,6-Dimethyl)Tyr-Lys-Phe-NH2 (I) and further salifying it with acetic acid to form the corresponding salt.

2. A process according to claim 1 wherein the coupling between (II) and (III) and/or the coupling between (VI) and (VII) and/or the coupling between (IX) and (X) is performed in the presence of N,N,N',N'-tetramethyl-O-(benzotriazol-1-yl)uronium tetrafluoroborate.

3. A process according to claim 2 wherein the coupling between (II) and (III) and/or the coupling between (VI) and (VII) and/or the coupling between (IX) and (X) is performed in the presence of a tertiary amine, preferably selected from N-methyl morpholine, triethylamine or diisopropylethylamine.

4. A process according to claim 1 wherein the coupling between (II) and (III) and/or the coupling between (VI) and (VII) and/or the coupling between (IX) and (X) is performed in organic polar solvents.

5. A process according to claim 1 wherein the coupling between (II) and (III) is performed in a temperature range between 0° C. and 60° C.

6. A process according to claim 1 wherein the formation of methanesulfonic salt (VI) is obtained in methylene chloride as solvent and crystallized from the same solvent.

7. A process according to claim 1 wherein the coupling between (VI) and (VII) is performed in a temperature range between 0° C. and 60° C.

8. A process according to claim 1 wherein the coupling between (IX) and (X) is performed in a temperature range between 0° C. and 60° C.

9. A process according to claim 1 wherein the step of deprotecting compound (XI) is performed by hydrogenation.

10. A compound of formula (VIII): Boc-(2,6-dimethyl)Tyr(Bzl)-Lys(Z)-Phe-NH2

11. A compound of formula (XIV) H-(2,6-dimethyl)Tyr(Bzl)-Lys-Phe-NH2 or a salt thereof:

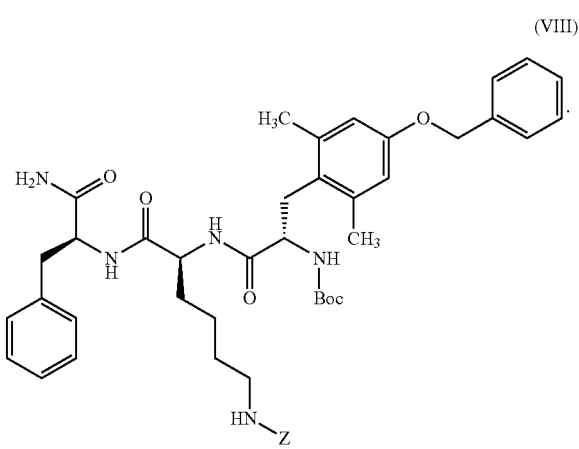

(VIII)

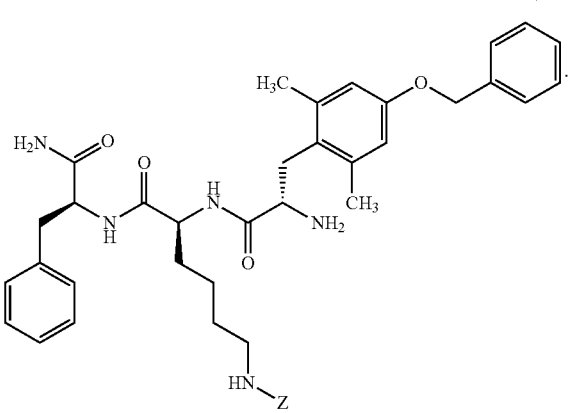

(XIV)

12. A compound according to claim 11 in form of the mesylate salt.

13. A compound of formula (XI) Z-D-Arg-(2,6-dimethyl)Tyr(Bzl)-Lys(Z)-Phe-NH2

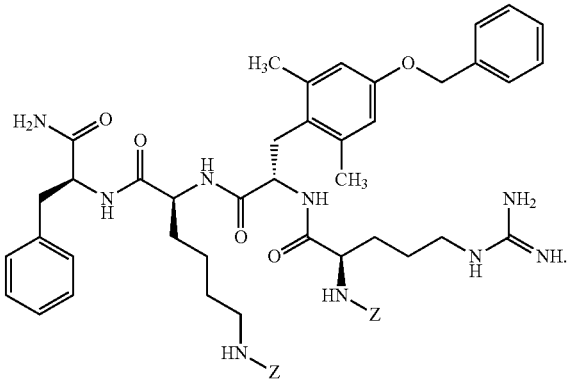

(XI)

14. A process according to claim 4, wherein said organic polar solvents is selected from dimethylformamide, acetonitrile, tetrahydrofuran, 2-methyl tetrahydrofuran, or a mixture thereof.

* * * * *